(12) United States Patent
Matsuno et al.

(10) Patent No.: US 8,308,743 B2
(45) Date of Patent: Nov. 13, 2012

(54) CLIPPING DEVICE

(75) Inventors: Kiyotaka Matsuno, Sagamihara (JP); Koh Kimura, Yokohama (JP)

(73) Assignee: Olympus Corporation, Tokyo (JP)

( * ) Notice: Subject to any disclaimer, the term of this patent is extended or adjusted under 35 U.S.C. 154(b) by 1073 days.

(21) Appl. No.: 10/072,721

(22) Filed: Feb. 6, 2002

(65) Prior Publication Data

US 2002/0173805 A1 Nov. 21, 2002

(30) Foreign Application Priority Data

Feb. 6, 2001 (JP) ................................. 2001-029839

(51) Int. Cl.
*A61B 17/10* (2006.01)
*A61B 17/08* (2006.01)
*A61D 1/00* (2006.01)

(52) U.S. Cl. .................... 606/142; 606/151; 606/221

(58) Field of Classification Search .............. 606/142, 606/151, 184, 158, 221; 24/543, 549; 206/363, 206/438
See application file for complete search history.

(56) References Cited

U.S. PATENT DOCUMENTS

| | | | |
|---|---|---|---|
| 2,600,091 A | 6/1952 | Becker | |
| 3,958,576 A * | 5/1976 | Komiya | 606/142 |
| 4,367,746 A * | 1/1983 | Derechinsky | 606/142 |
| 4,681,107 A | 7/1987 | Kees, Jr. | |
| 4,834,702 A | 5/1989 | Rocco | |
| 5,242,456 A * | 9/1993 | Nash et al. | 606/142 |
| 5,499,990 A * | 3/1996 | Schulken et al. | 606/144 |
| 5,520,701 A * | 5/1996 | Lerch | 606/142 |
| 5,766,184 A * | 6/1998 | Matsuno et al. | 606/142 |
| 5,766,189 A * | 6/1998 | Matsuno | 606/158 |
| 5,993,465 A * | 11/1999 | Shipp et al. | 606/142 |
| 5,993,474 A * | 11/1999 | Ouchi | 606/206 |
| 6,090,129 A * | 7/2000 | Ouchi | 606/206 |
| 6,814,742 B2 * | 11/2004 | Kimura et al. | 606/151 |
| 7,094,245 B2 * | 8/2006 | Adams et al. | 606/142 |

FOREIGN PATENT DOCUMENTS

| | | |
|---|---|---|
| DE | 24 54 371 | 6/1975 |
| DE | 695 17 153 T2 | 5/1996 |
| DE | 197 07 382 A1 | 9/1997 |
| JP | 53-20957 | 6/1978 |
| JP | 62-189060 A | 8/1987 |
| JP | 8-280701 | 10/1996 |
| JP | 08-280701 A | 10/1996 |
| JP | 2000-175925 | 6/2000 |
| JP | 2001-520069 A | 10/2001 |
| JP | 2002-224124 | 8/2002 |

OTHER PUBLICATIONS

Japanese Office Action dated Oct. 6, 2009 with English Translation.

(Continued)

*Primary Examiner* — Gary Jackson
*Assistant Examiner* — Michael Mendoza
(74) *Attorney, Agent, or Firm* — Scully, Scott, Murphy & Presser, PC (57) ABSTRACT

The present invention provides a clipping device having a coil sheath inserted into an insertion tube in a back/forth movable way to allow it to be inserted into a body cavity, an operation wire inserted into the coil sheath in a back/forth movable way, and a clip directly connected to a distal end of the operation wire to allow it to clip a living tissue.

24 Claims, 8 Drawing Sheets

OTHER PUBLICATIONS

Japanese Office Action dated Oct. 13, 2009 with English Translation.
Japanese Office Action dated Apr. 26, 2011 together with English translation.

Japanese Office Action dated May 22, 2012 from corresponding Japanese Patent Application No. 2010-132264 together with an English language translation.

* cited by examiner

CLIPPING DEVICE

CROSS-REFERENCE TO RELATED APPLICATION

This application is based upon and claims the benefit of priority from the prior Japanese Patent Application No. 2001-029839, filed Feb. 6, 2001 the entire contents of which are incorporated herein by reference.

BACKGROUND OF THE INVENTION

The present invention relates to a clipping device for performing an operation, such as stopping bleeding, in living tissue with the use of a clip.

The clipping device disclosed in Jpn. Pat. Appln. KOKAI Publication No. 8-280701 has an operation tube slidably located into an insertion tube and a coupling ring fixedly mounted on the distal end of the operation tube to hold a clip unit in place. In this publication, a hook member is connected to the distal end of an operation wire inserted into the operation tube and the clip unit is detachably latched to the hook member. Since, in this clipping device, the clip unit was detachably mounted on a device body, it was necessary to perform an operation of mounting the clip unit to the hook member of the device body each time the clip was used. The clip unit itself was very small in size and it was cumbersome to latch a coupling plate of the clip unit to the hook member fixed to the distal end of the operation wire. The mounting operation of the clip unit was cumbersome and it took a lot of time to prepare the clipping device for actual use.

Further, after the clipping, the coupling member separated from the clip was sometimes dropped in the body cavity. When the coupling member was dropped in the body cavity, it was necessary to perform an operation such as removing it to an outside. However, the coupling member itself was very small, thus making it difficult to find. In addition, the removal operation was also cumbersome. These operations took a long time to perform, thus placing a greater burden was placed on the patient.

After the clipping operation, the clip is separated from the coupling member by strongly pulling the operation wire. At this time, by exerting a strong pull force exceeding a given force on the operation wire, the hook section of the coupling plate of the clip unit is elongated to a full extent and the clip is separated by doing so. Since the clip is separated from the rest of the device with the hook section of the coupling plate elongated to the full extent, if a pull force on the hook section is released the instant the clip is separated off the coupling plate, then the operation wire on which such a strong pull force has thus far been exerted is drawn into the coil sheath and also the hook member is drawn deep into the coil sheath. If the hook member is so drawn deep into the coil sheath, then it takes a long time to mount a new clip unit on the rest of the device.

The hook member fixed to the distal end of the operation wire is usually made of a rigid member so as to secure its strength. For this reason, the length of the rigid section area near that distal end is made longer by the amount of the rigid member and the insertion operation into the endoscope becomes more cumbersome with a resultant disadvantage.

As endoscopes, the so-called side viewing and oblique viewing scope are known and, in these types, the clipping device is projected in a side or oblique direction from such a type of endoscope. If, therefore, the length of the rigid section area near the distal end section is made greater, the insertion operation into the endoscope becomes much more cumbersome.

Further, where the clipping device is used in combination with the side viewing and oblique viewing scopes, the coil sheath into which the hook member is drawn is tightly bent, so that the hook member is liable to be deformed when it is drawn into the coil sheath. When the hook member is so deformed, then it becomes difficult to mount a new clip on the device body. It has, therefore, been considered difficult to use the clipping device in combination with side viewing and oblique viewing scopes.

Further, the coupling method of the clip and device body poses a problem such as the dropping of the clip out of the device body due to vibration or drop page during a transport, etc. At this time, it is necessary to perform an operation such as, again, mounting the clip on the device body.

BRIEF SUMMARY OF THE INVENTION

An object of the present invention is to provide a clipping device which, upon removal from a pack, can be immediately used.

A further object of the present invention is to provide a clipping device which prevents a drop of a coupling member for latching a clip.

Another object of the present invention is to provide a clipping device which ensures a better insertability into an endoscope.

A further object of the present invention is to provide a clipping device which can be easily used under in combination with a side viewing or oblique viewing scope.

In order to achieve the above-mentioned object, there is provided a clipping device comprising a sheath member insertable into a body cavity of a subject, an operation wire inserted into the sheath member in a back/forth movable way, a coupling member directly connected to a distal end of the operation wire, and a clip for use in clipping a living tissue, the clip being detachably coupled to the coupling member and adapted to be closed by a pulling operation of the operation wire.

The clipping device is such that the operation wire and coupling member are so fixed as to be nondetachable.

The clipping device is such that the operation wire and coupling member are connected to each other by passing the operation wire into a hole of the coupling member and doubling the operation wire back upon itself on its part way, so that the operation wire and clip unit are connected to each other.

Further, the present invention provides a clipping device comprising a clip retainable in a living tissue, an insertion member for introducing a clip into the living body cavity, and an operation mechanism capable of performing an operation of retaining the clip onto the body cavity, in which, when the device is packaged, at least one clip is mounted on the insertion member.

Further, the clipping device is such that it has a twice inadvertent clip attachment prevention feature which, when one clip initially mounted on the insertion member has been used and retained onto the body cavity, another clip cannot be again mounted and so used.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A clipping device according to a first embodiment of the present invention which is used for an endoscope will be described below with reference to FIGS. 1 to 6.

Figure 1A:
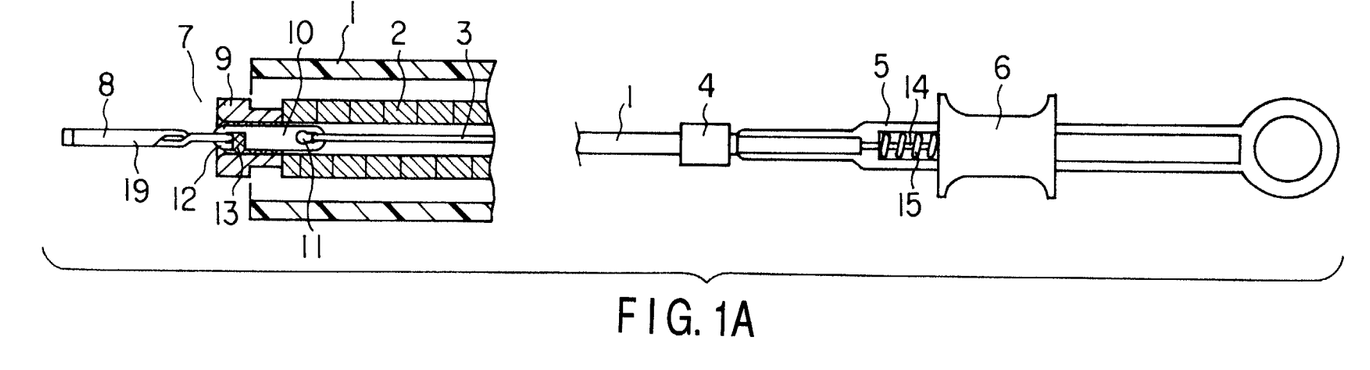
FIG. 1A is an explanatory view, partly in cross-section, showing a distal end section, in an enlarged form, of a clipping device according to a first embodiment of the present invention for use in an endoscope.

As shown in FIG. 1A, the clipping device according to the embodiment which is used for the endoscope is constructed such that its member introduced into a body cavity of a subject comprises an insertion tube 1 comprised of a high density polyethylene tube, etc., and has an inner/outer diameter size of about $\phi$2.1 mm/2.5 mm and a coil sheath 2 serving as a sheath member, inserted into the insertion tube 1 in a way to be movable back and forth. Into the coil sheath 2 an operation wire 3 made of, for example, stainless steel is inserted in a way to be movable back and forth and is covered with high density polyethylene. An operation section is provided near a base end of the insertion tube 1 fitted over an outer periphery of the coil sheath 2. The operation section comprises a silicone grip (first operation means) 4 so mounted as to be press-fitted over the base end portion of the insertion tube 1 and adapted to move the insertion tube 1 back and forth relative to the coil sheath, an operation section body 5 provided on the base end of the coil sheath 2 and a slider (second operation means) 6 mounted at the base end of the operation wire 3 through a pipe 14 and slidable relative to the operation section body 5. A clip unit 7 as will be set out below is mounted on a distal end of the operation wire 3. On the operation wire 3 a silicone oil is coated so as to improve the slidability relative to the coil sheath 2.

Figure 1B:
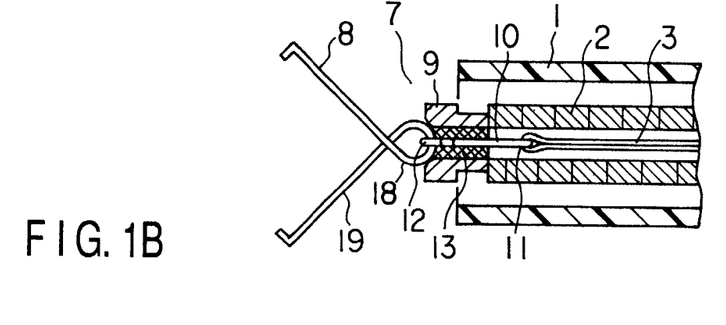
FIG. 1B is a cross-sectional view showing a distal end section, in an enlarged form, of the clipping device according to the first embodiment of the present invention.

The clip unit 7 as set out above comprises a claw-like clip 8, a holding-down tube 9 and a coupling plate 10 serving as a coupling member. The clip 8 is so bent as to have an α shape at an intermediate portion of its elastic plate-like member and a claw at each end of its elastic plate-like member. The clip 8, being in its natural state released from an associated part, has its arm portions 19 opened under its own elastic resilience force to a relatively small extent as shown in FIG. 1B.

The coupling plate 10 has a through hole 11 extending through a proximal side end portion and a hook section 12 at a distal side end to engage the clip 8. The hook section 12 is anchored, in the holding-down tube 9, to the looped portion (a portion 18) of the base end side of the clip 8. In this state, a filling material such as silicone 13 is filled into the holding-down tube 9 to mount the clip 8 to the hook section 12, so that the clip 8 is prevented from being removed from the hook section. At this time, the a portion 18 of the clip 8 is not retracted deep into the holding-down tube 9 and it is, therefore, possible to spread the arm portions 19 of the clip 8 apart as shown in FIG. 1B.

The operation wire 3 passes through the hole 11 of the coupling plate 10 and has its intermediate portion doubled back upon itself. By doing so, the so double-back end portions of the operation wire 3 extend in a parallel fashion and are inserted in the coil sheath 2 in a back/forth movable way. Both the base end portions of the operation wire 3 are coupled to the slider 6 of the operation section. The pipe 14 is fitted over both the doubled-back end portions of the operation wire 3. The doubled-back portions of the operation wire 3 are very tightly bent and, under a bent-back pressure force, anchor the coupling plate 10 therebetween and are fixed to the coupling plate 10.

The insertion tube 1 has its outer surface embossed to provide a fine uneven surface. By doing so, a contact surface between the insertion tube 1 and a channel of an endoscope is reduced to provide an improved insertability of the insertion tube into the channel of the endoscope. Further, the insertion tube 1 has its inner surface also embossed to reduce the sliding resistance between the insertion tube 1 and the coil sheath 2.

At an area positioned between the operation section body 5 and the slider 6, a compressed spring 15 is wound loosely around an outer periphery of the pipe 14. Under the elastic force of the spring 15, the slider 6 is urged toward the proximal side and no separation is made between the distal end of the coil sheath 2 and the base end surface of the holding-down tube 9. By doing so, at the time of use and at the time of transport, there occurs no deformation of members, such as the coupling plate 10, at a remote side.

Figure 2:
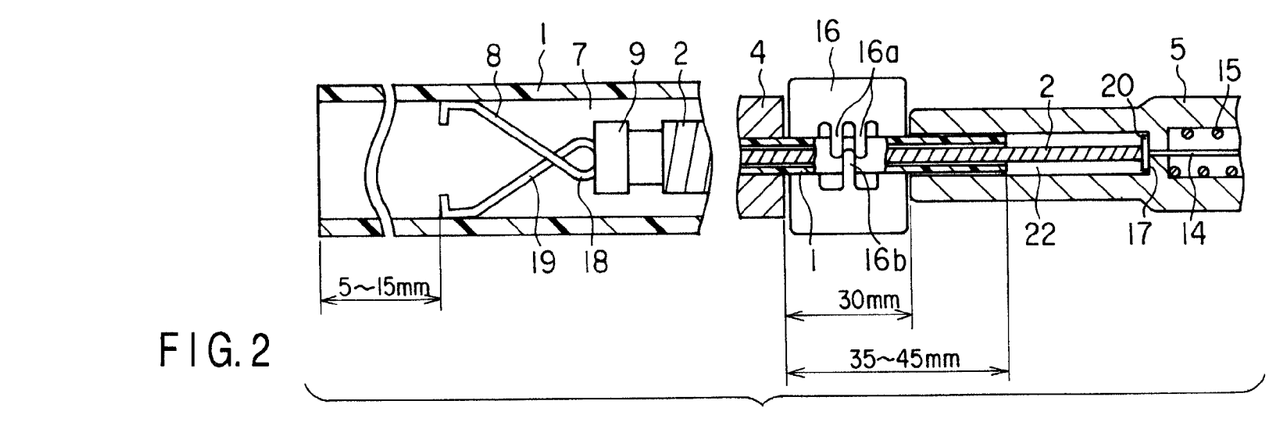
FIG. 2 is a view in longitudinal cross-section showing a state involved when the clipping device according to the first embodiment of the present invention is packaged.
Figure 6:
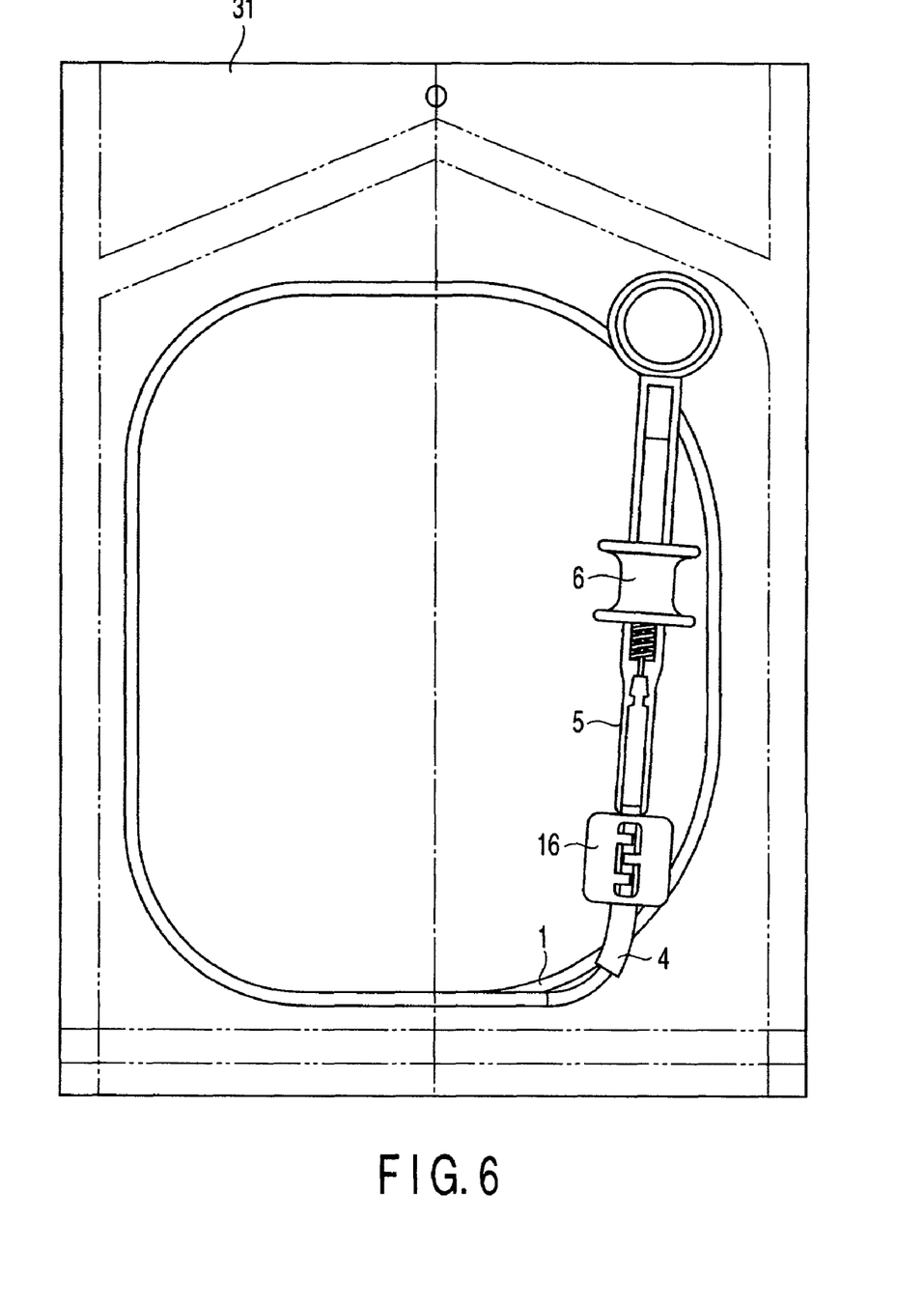
FIG. 6 is an explanatory view showing a state in which the clipping device according to the first embodiment of the present invention is packaged in a pack.

As shown in FIG. 2, the base end surface of the coil sheath 2 is so formed as to be held by a receiving section 17 of the operation section body 5. In order to prevent the coil sheath 2 from piercing the receiving section 17 when a very large force acts thereon, a washer 20 made of a metal is inserted between the base end surface of the coil sheath 2 and the receiving section 17 of the operation section body 5.

Where a resultant clipping device is packaged as a product, the clipping device as a whole is so packaged by a unit pack. As shown in FIG. 6 for example, a sterilized pack 31 is used as the unit pack. The clipping device is sealed wholly in a coiled form into the sterilized pack 31 and is subjected to a sterilizing process. At this time, as shown in FIG. 2, the distal end of the clip 8 is retracted about 5 to 15 mm back from the distal end of the insertion tube 1 and, in this state, the clipping device is loaded into the sterilized pack. With the clipping device wholly loaded in the sterilized pack 31, it is inserted in a carton and is ready for distribution. In order to prevent the insertion tube 1 from moving toward its proximal side due to vibration/falling during the transport, etc., and hence to prevent the clip 8 from projecting from the insertion tube 1 relative to the coil sheath 2, a spacer 16 is fitted between the grip 4 and the distal end of the operation section body 5 as shown in FIG. 2 to prevent a distance between the grip 4 and the operation section body 5 from being shortened by more than given extent.

Figure 5:
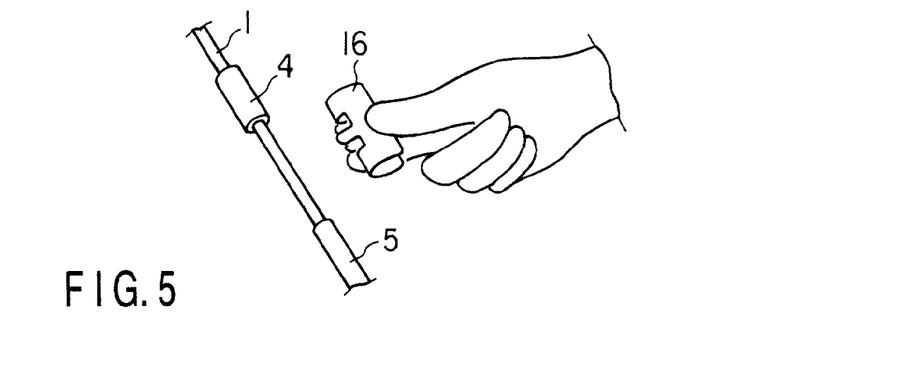
FIG. 5 is an explanatory view showing a state in which, when the clipping device according to the first embodiment of the present invention is used, a spacer is removed from an insertion tube.

The spacer 16 is comprised of a bendable plate-like member having mutually latching tongue pieces 16a, 16b at its middle portion. As a material of the plate-like member, use is made of, for example, a resin member such as polypropylene. As shown in FIG. 5, the latching tongue pieces 16a, 16b are fitted on the outer periphery of the insertion tube 1 and detachably mounted on the insertion tube 1.

As shown in FIG. 2, where the clip 8 as set out above is held at a predetermined place in the insertion tube 1, the grip 4 is spaced about 30 mm from the distal end of the operation section body 5 and, at a position of that range, the spacer 16 is fixedly press-fitted on the insertion tube 1. A distance of about 35 to 40 mm is set from the base end surface of the grip 4 to a base end surface of the insertion tube 1. That is, the base end of the insertion tube 1 is inserted in the operation section body 5 to a depth of 5 to 10 mm in a space 22 relative to a coil sheath 2.

The above-mentioned sizes are only an example, and can be varied depending upon the kind, etc., of clipping device and they are not restricted thereto.

An explanation will be made below about how to use the clipping device with the endoscope. With the clip 8 held in the insertion tube 1 as shown in FIG. 2, the insertion tube 1 of the clipping device is inserted into a channel of an endoscope initially inserted into a body cavity of a subject. After the distal end of the insertion tube 1 projects into the body cavity, the spacer 16 is picked up and, by bending it in a U-shaped configuration, removed out of the insertion tube 1 as shown in FIG. 5.

Then, the insertion tube 1 is pulled by the grip 4 toward the proximal side and the clip 8 is projected from the distal end of the insertion tube 1 (see FIGS. 1A and 1B). At this time, the base end of the insertion tube 1 is held in the operation section body 5. That is, the coil sheath 2 is set to a state in which it is not exposed to an outside. Therefore, the projecting operation of the clip 8 is done very smoothly. Assuming that the coil sheath 2 is exposed to an outside, the coil sheath 2 is bent at that portion, failing to project the clip 7 smoothly. According to the present invention, it is possible to avoid this situation.

Figure 3:
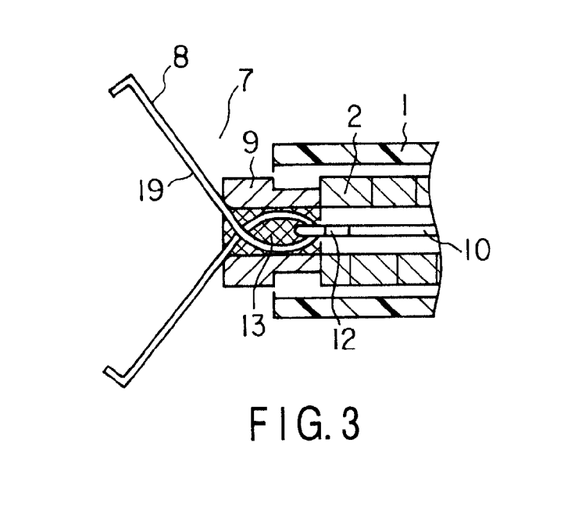
FIG. 3 is a view in longitudinal cross-section showing a clip held near the distal end section of the clipping device according to the first embodiment of the present invention.

Then, by pulling the slider 6, with a slight force, toward the proximal side, the a portion 18 of the clip 8 is drawn into the holding-back tube 9 as shown in FIG. 3 and the arm portions 19 of the clip 8 are more largely spread apart. In this state, the insertion tube 1 which has been projected toward the proximal side of the endoscope is pushed forward and the distal ends of the spread-apart claws are pushed onto a bleeding site, etc., of interest in the body cavity of a subject.

Figure 4:
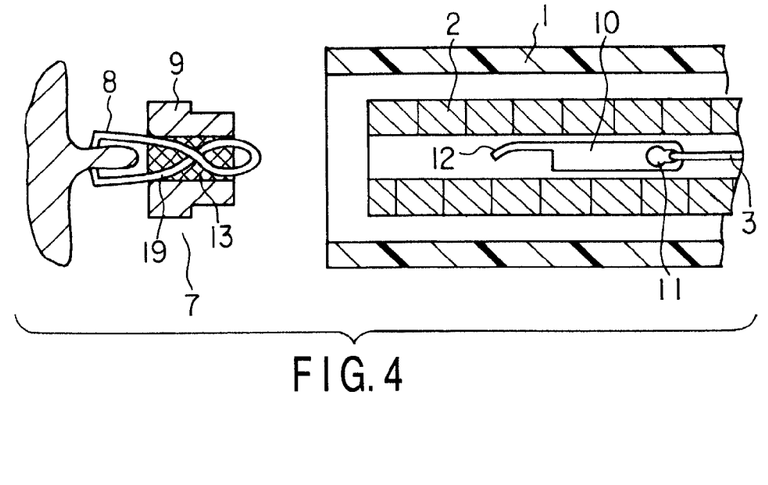
FIG. 4 is an explanatory view showing a state in which, after the clipping device according to the first embodiment of the present invention is used, the clip is separated from the rest of the device while grasping a tissue.

When, from a state shown in FIG. 3, the slider 6 is strongly pulled toward the proximal side, then the base end portions of the arm portions 19 of the clip 8 are retracted into the holding-down tube 9 and, as shown in FIG. 4, the arm portions 19 are closed to the tissue at a bleeding site to be grasped.

When the slider 6 is more strongly pulled, the hook section 12 of the coupling plate 10 is extended and the clip 8 is detached. The tissue is put in a grasped state by only the holding-down tube 9 and clip 8 in the clip unit 7. With the tissue grasped by the clip 8, the clip 8 is detached from the device body and placed in a state as shown in FIG. 4. The clip 8 is placed in a bleeding site-grasped state for about one week and kept within the body cavity, thus stopping the bleeding at that site.

In order to realize the above function, the strength, etc., of the hook section 12 is so set as to allow it to be extended after the clip 8 has been retracted into the holding-down tube 9 and put to a state in which the tissue can be adequately grasped. That is, after the use of one attached clip, another clip 8 cannot be attached again to the clipping device to provide a twice inadvertent clip attachment prevention feature. As such a feature, use may be made of other means, such as a stopper, for preventing another clip from being inadvertently attached.

In this embodiment, the operation wire 3 and coupling member 10 are so formed as to provide a non-detachable structure. Therefore, there is no possibility that, even after the clipping of the bleeding site by the clip 8, the coupling member will drop in the body cavity. By doing so, it is not necessary to make any collection operation of the coupling member 10. And it is possible to largely reduce an operator's manual operation time and to alleviate the burden on the patient.

Further, the present clipping device is packaged with a clip 8 attached to that device body. The clipping device is sterilized/packaged with a clip 8 held in its insertion tube 1 or sterilized with these packaged by a sterilized pack. In either case, the clipping device is packaged/shipped as a sterilized product. Since the clipping device is provided as a sterilized-state product, it is not necessary to perform any cumbersome attaching operation of the clip 8 and it is possible to immediately use the clip if the product is unpacked. Further, since the doubled-back operation wire 3 is positively fixed to the coupling plate 10 past the hole 11, it is possible to eliminate the problem such as the clip 8 detaching from the device body during transport and handling in their attached state.

The medical operator, after the unpacking of the product, can immediately insert the insertion tube 1 into the channel of an endoscope and insert it into a body cavity and do so without the need of attaching a clip unit 7 to the device body. By doing so it is possible to use the clipping device as it is. If the clipping device is used at all, there is often the case that bleeding occurs in the body cavity of the patient and an emergency treatment is necessary. In such a situation, it was cumbersome to mount the clip unit 7 to the device body. According to the present invention, since the clip unit 7 is initially attached to the insertion member 1, if the product is unpacked, it is possible to immediately use it and to very efficiently and promptly perform a treating operation.

Since it is not necessary to perform a mounting operation of a clip unit 7 at a time of use, it is possible to obviate the necessity for using a pipe to be mounted on the distal end of the coil sheath so as to guide a clip 8, that is, a clip provided in the conventional technique, and to hence obviate the necessity for joining the pipe to the coil sheath and to obtain a low cost device.

Further, since the coupling member and above-mentioned pipe are not employed, the resultant device can be inserted with a slight amount of force into an associated endoscope (including a side viewing scope and oblique viewing scope). Still further, even under a combined use of the side viewing and oblique viewing scope, no burden is placed on the device body since the coupling device and above-mentioned pipe are not used.

In the case of a fixing system of the present invention, the clip unit 7 and device body are often of a one-time disposable type and it is not necessary to use an expensive coupling member (hook) of a complicated configuration and also join the coupling member (hook) to the wire by means of brazing, etc. It is, therefore, possible to provide a low cost device.

Figure 7:
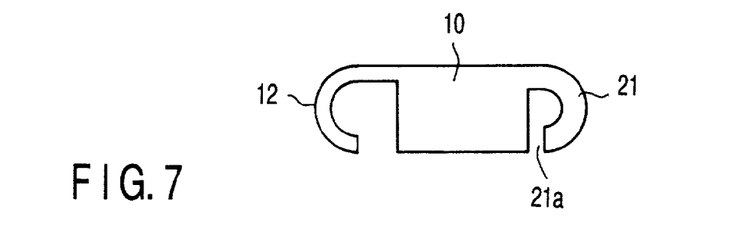
FIG. 7 is a plan view showing a coupling plate of a clipping device according to a second embodiment of the present invention for use in an endoscope.

A clipping device according to a second embodiment of the present invention for use in an endoscope will be explained below by referring to FIG. 7.

This embodiment is different from the first embodiment in that a hole formed at a proximal side end of a coupling member 10 is used as a hook 21. The remaining structure is the same as that of the first embodiment. The hook 21 is adequately higher in elongation strength than a distal end side hook section 12 of the coupling plate 10. Further, the width of an opening 21a of the hook 21 is made somewhat narrower than a diameter of the operation wire 3.

This embodiment is different from the first embodiment in that a clip 8 is detachable. After the clipping of an initially attached clip 8, a slider 6 is pushed until it abuts against a forward end. By doing so, doubled-back portions of the operation wire 3 are projected from the distal end of a coil sheath 2 and the coupling plate 10 is detached from the operation wire 3 by utilizing the elasticity of the hook 21 of the coupling plate 10. After this, by also utilizing the elasticity of the hook 21, the opening 21a is spread apart and a new clip 8 is inserted in the doubled-back portions of the operation wire 3 to attach it to the wire.

Incidentally, the average number of clips 8 required for stopping bleeding is three. For the case of attaching a second clip 8 it is necessary to perform a cumbersome operation, but it is possible to stop the bleeding in one patient by the use of one device body. According to the present invention, by forming a hole of the coupling plate 10 of a clip unit 7 as a hook-like hole it is possible to exchange only a clip 8 and, by doing so, to repeatedly use the device. The other advantages are the same as those of the first embodiment.

A clipping device according to a third embodiment for use in an endoscope will be explained below by referring to FIGS. 8 to 15.

This embodiment is different from the first embodiment in terms of a coupling plate 10, operation wire 3, operation section body 5, slider 6 and clip unit 7 only. The other structure is the same as that of the first embodiment set out above.

Figure 8A:
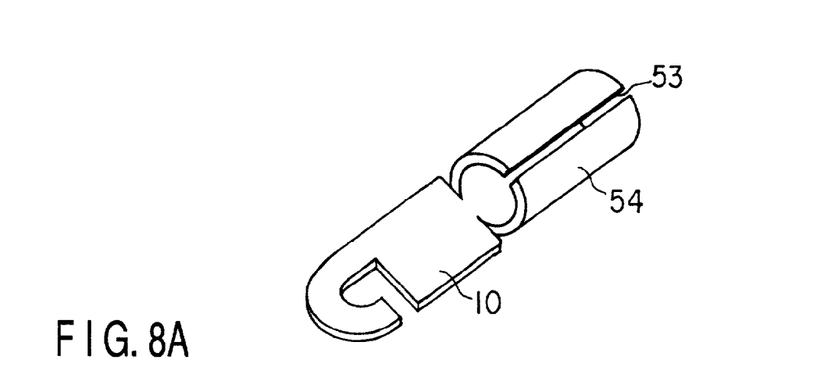
FIG. 8A is a perspective view showing a coupling plate of a clipping device according to a third embodiment of the present invention for use in an endoscope.
Figure 8B:
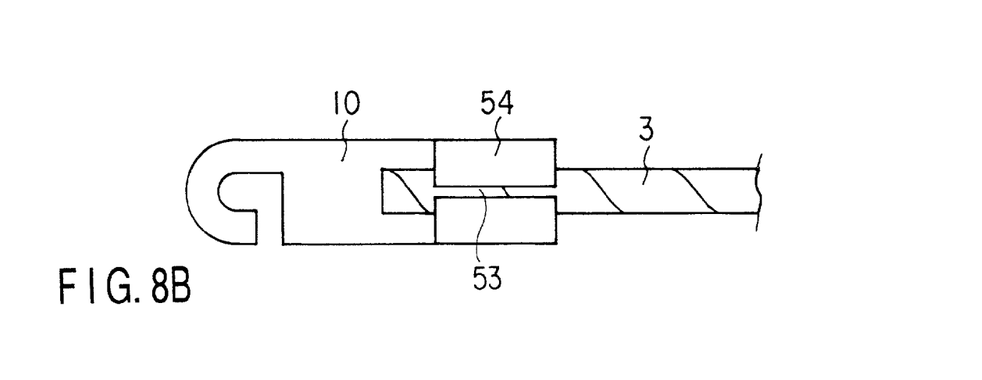
FIG. 8B is a plan view showing the coupling plate coupled to an operation wire.
Figure 9:
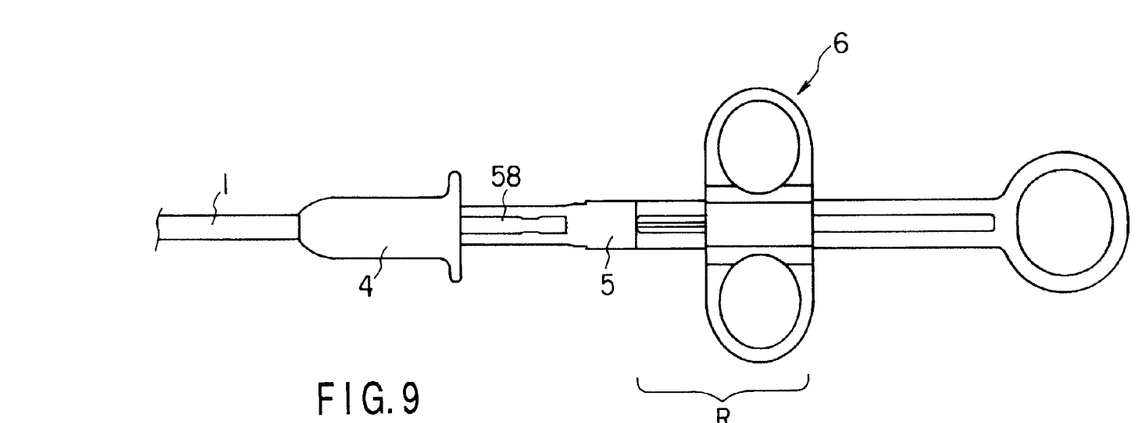
FIG. 9 is a plan view showing an operation section of the clipping device according to a third embodiment of the present invention.

In this embodiment, as shown in FIG. 8A, a substantially tube-like fixing section 54 having a slit 53 is provided at a proximal side end portion of the coupling plate 10 and, as shown in FIG. 8B, the distal end portion of the operation wire 3 is passed through the tube-like fixing section 54 and, by the press-fitting of the fixing section 54, the distal end portion of the operation wire 3 is fixed to the fixing section 54.

The fixing of the operation wire 3 and fixing section 54 may be done by means of laser welding, brazing, etc. It is desirable to set the length of the fixing section 54 to below 30 mm from the standpoint of a consideration of the insertability into the endoscope.

Figure 10A:
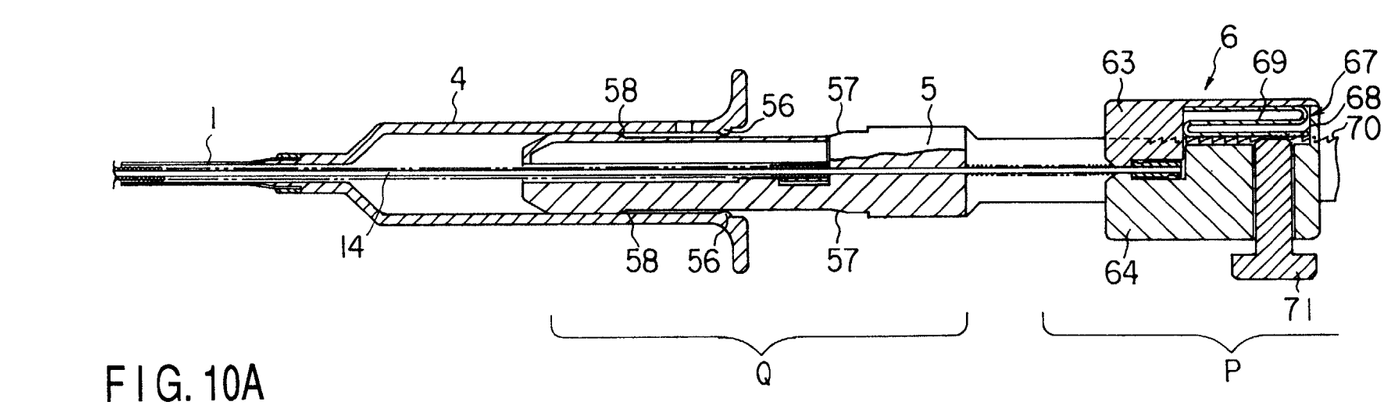
FIGS. 10A and 10B each show an operation section of the clipping device according to the third embodiment of the present invention.
Figure 10B:
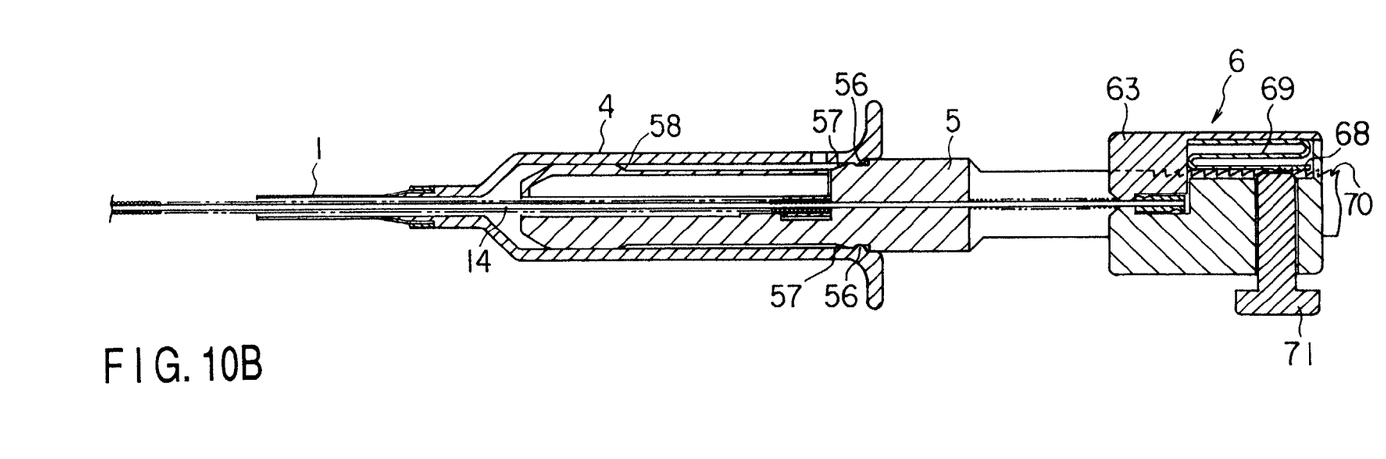

A grip 4 is formed of a molded resin such as ABS, etc., and, as shown in FIG. 10A, with the distal end side portion of the grip 4 set in a state connected to the base end portion of the insertion tube 1, the grip is fitted relative to the operation section body 5 in a back/forth movable way. A projection 56 is provided on the inner surface portion of a proximal side of the grip 4. By pulling the grip 4 toward the proximal side, an inclining surface portion 57 on the outer periphery of a distal end portion of the operation section body 5 is press-fitted onto the projection 56 as shown in FIG. 10B and, by doing so, the grip 4 can be fixed to the operation section body 5. When the grip 4 is pushed ahead, the projection 56 is press-fitted on another inclining surface portion 58 provided on the outer periphery of the operation section body 5 and, similarly, the grip 4 can be fixed to the operation section body 5. The outer diameter of the operation section body 5 situated between the inclining surface portion 57 and the inclining surface portion 58 is smaller than each end side and provides a reduced-diameter outer peripheral portion.

Figure 12:
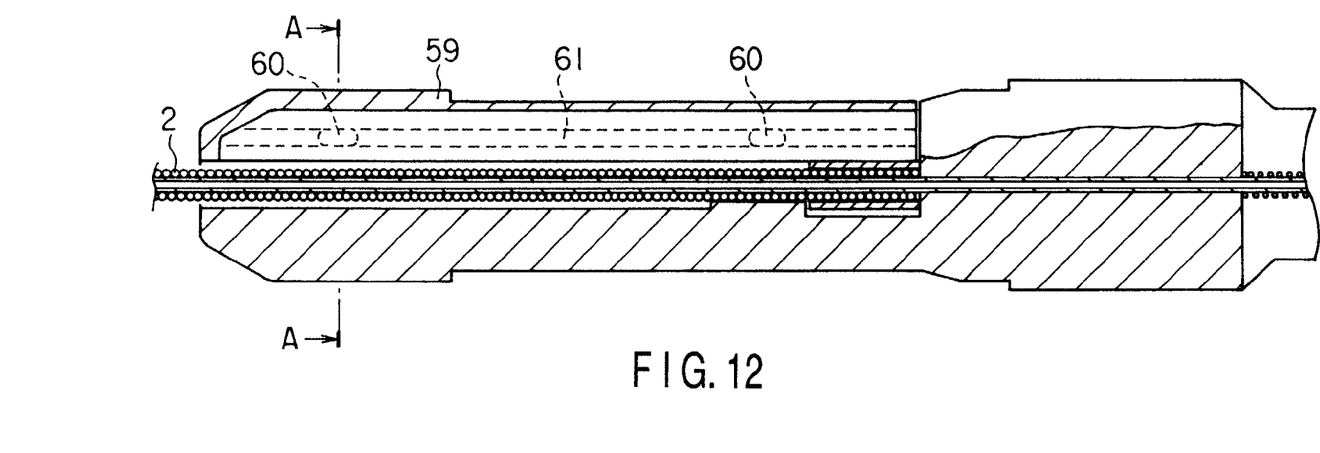
FIG. 12 is a view in longitudinal cross-section showing a portion Q of FIG. 10A enlarged.
Figure 13:
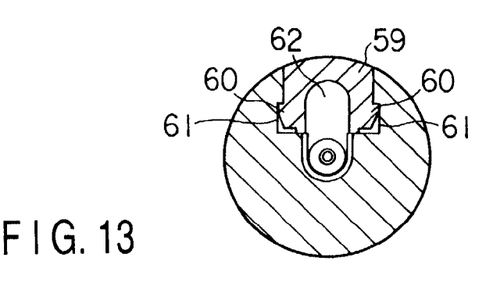
FIG. 13 is a transverse cross-section showing a portion, in an enlarged form, taken along line A-A of FIG. 12.

As shown in FIGS. 12 and 13, the proximal side portion of the coil sheath 2 is located at the operation section body 5 and, after the fixing of the coil sheath 2 and operation section body 5, the proximal side portion of the coil sheath 2 is covered with a body cover 59. Claw sections 60 are provided on the body cover 60 and, by the engagement of the claw section 60 with an associated engaging groove 61 provided in the operation section body 5, the body cover 59 is fixed.

As shown in FIG. 13, a groove 62 semi-circular in cross-section is provided in the body cover 59 and serves as a clearance for allowing the body cover 59 to be elastically deformed when the claw section 60 engages the associated groove 61.

Figure 14:
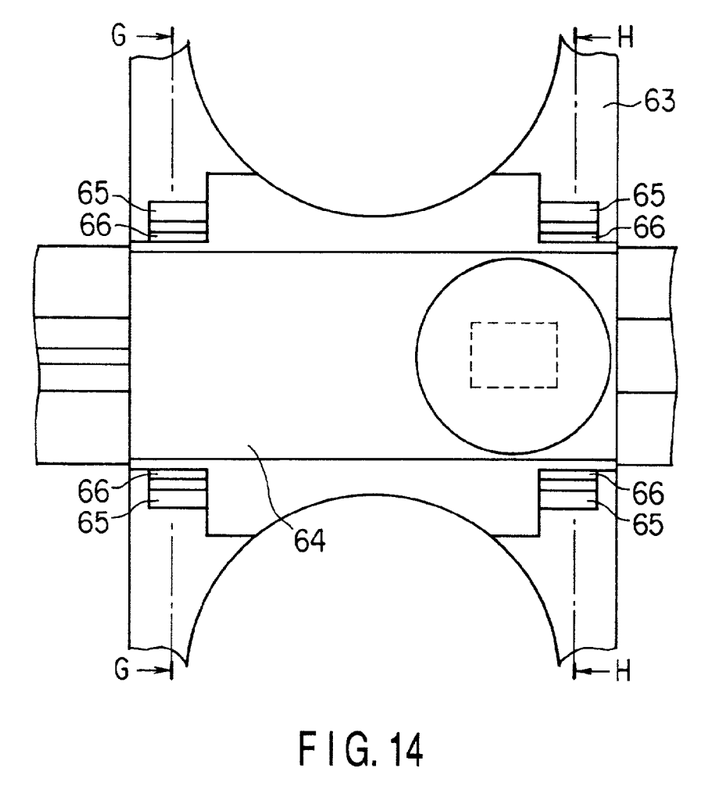
FIG. 14 is a plan view showing a portion R of FIG. 9 enlarged.
Figure 15:
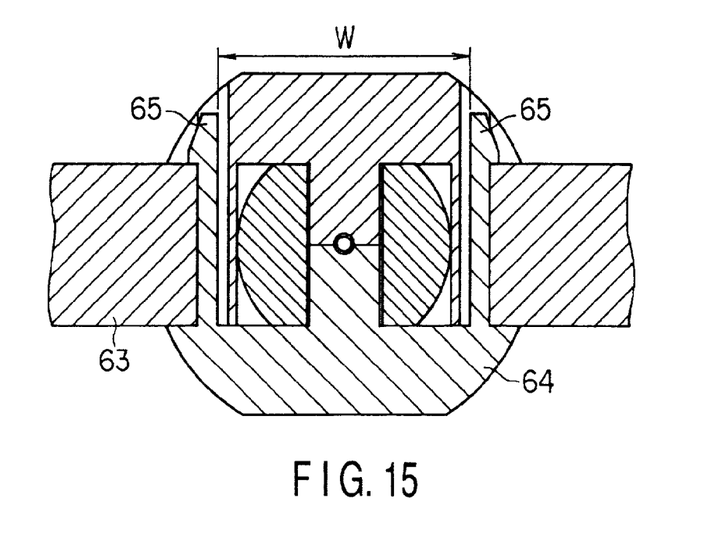
FIG. 15 is a transverse view taken along line G-G and line H-H of FIG. 14.

As shown in FIGS. 10A and 14, the slider 6 comprises a slider body 63 and slider cover 64. Four engaging claws 65 in total are provided on the slider body 63. The slider cover 64 has an engaging hole 66 at a position corresponding to an interval W of the engaging claws 65 on the slider body 63 as shown in FIG. 15 and, by inserting the engaging claw 65 of the slider body 63 into the corresponding engaging hole 66 of the slider cover 64, the engaging claw 65 engages the engaging hole 66 so that these are fixed together.

Figure 11:
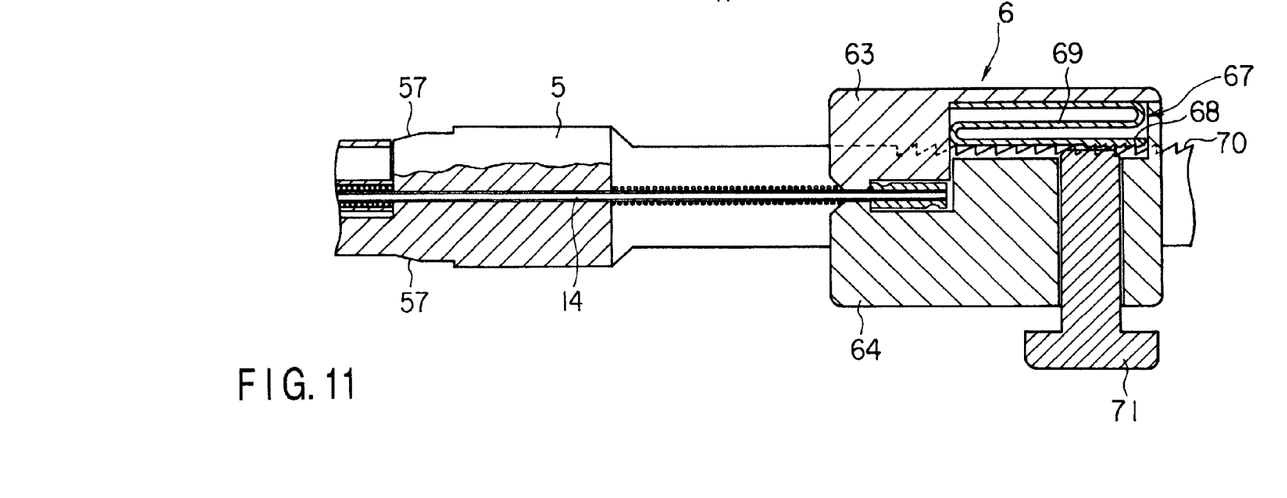
FIG. 11 is a view in longitudinal cross-section showing a portion P of FIG. 10A enlarged.

Further, as shown in FIG. 11, a ratchet pawl 67 is provided on the slider 6. The ratchet pawl 67 is comprised of an integral unit of latching means 68 and elastic section 69 which is one piece molded with the use of a resin such as ABS. By the elastic section 69, the latching means 68 is normally urged against the operation section body 5. The operation section body 5 has a latching claw 70. The latching claw 70 engages the latching means 68 to latch the slider 6 from moving toward a distal end side. The slider 6 has a ratchet release button 71 and, by depressing the ratchet release button 71, the latching means 68 is pushed away from the latching claw 70 and the slider 6 can be moved toward the distal end side.

Figure 16:
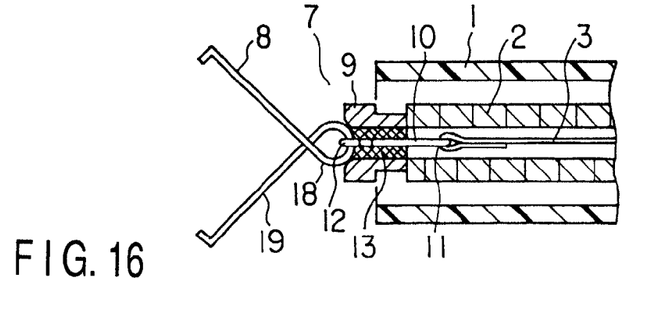
FIG. 16 is a longitudinal view showing a distal end portion, in enlarged form, of the clipping device according to a third embodiment of the present invention.

Although, in the above-mentioned first embodiment, the operation wire 3 is doubled back upon itself at a distal end portion with both its ends fixed to the slider 6, only one end of the doubled-back portions of the operation wire 3 may be fixed to the slider 6 with the other end of the doubled-back wire portions fixed to said one end of the double-backed wire portions in a manner to extend partway along said one end thereof, as shown in FIG. 16.

The operation of this embodiment in use is the same as that of the first embodiment.

According to an aspect of this embodiment, where the coil sheath 2 and insertion tube 1 are operated in a back-forth moving way by operating the grip 4, it is possible to perform an operation under a given effect of feeling because there is a slight amount of force variation at the press-fitting of the projection 56 and inclining surface portion 57. Further, the fixing mechanism of the grip 4 and operation section body 5 is comprised of the projection 56 and inclining surface portion 57 and it is not necessary to use additional members and it is also possible to manufacture a device at a low cost. By the latching and fixing of the slider 6 it is possible to obviate the need to use an adhesive and perform a bonding operation, etc., and to manufacture an inexpensive device.

According to the above-mentioned product, a clip unit 7 is already incorporated into the device body and hence into the insertion tube and its packaged product is obtained in a sterilized state. By doing so, in order to use the clipping device, it need only be removed from the sterile packet, without involving any cumbersome operations, such as attaching a clip 8 to the rest of the device. Since the operation wire 3 is coupled to a coupling member 10 of the clip unit 7, there arises no problem such as the disengaging of a clip 8 from the device body during transport and handling in the assembled state. It is not necessary for the user to pick up a clipping device and attach a clip 8 to the device body and it is possible to immediately use it. Since the operation wire 3 is passed through the hole 11 of the coupling member 10 of the clip unit 7 and, by doubling the operation wire 3 back upon itself partway along its length, the operation wire 3 is coupled to the coupling member 10 of the clip unit 7, and the operation wire 10 can be positively connected to the coupling member 10 of the clip unit 7. In the case of connecting the operation wire 3 to the coupling member of the clip unit 7, the clip unit 7 and device body are thrown away only one at a time. In this case it is possible to eliminate the need to provide a coupling member such as a hook of a complicated configuration and a pipe, etc., mounted at a distal end of the coil sheath to guide a clip 8, these being used in the conventional technique. Further, it is not necessary to fixedly join the operation wire 3 to the coupling member 10 by means of brazing, etc. This enables a clipping device to be obtained at a low cost. Since the conventional coupling member and pipe are not employed, the present device can be inserted with a slight amount of force into an endoscope, including side viewing and oblique viewing scopes. Even under a combined use of the side viewing and oblique viewing scopes, no burden is placed on the device body since the conventional coupling member and pipe as set out above are not used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clipping device comprising:
   a sheath member to be inserted in the body of the patient;
   an actuating wire received in the sheath member so as to be longitudinally movable relative to the sheath member;
   a clip unit attached to the clipping device in advance and having a tissue clip for clipping in the body of the patient and a coupling member arranged at a distal end of the actuating wire;
   wherein:
   the coupling member includes a first end fastened to the distal end of the actuating wire to be immovable in an axial direction of the actuating wire and a direction deviating from the axial direction and a second end attached to the tissue clip; and
   when applying the tissue clip, the second end of the coupling member is deformable upon exertion of a force in a proximal direction at the first end of the coupling member that is greater than a predetermined amount so as to prevent a subsequent attachment of the second end to another tissue clip.

2. The clipping device according to claim 1, wherein the first end of the coupling member is directly fastened to a peripheral surface of the distal end of the actuating wire.

3. The clipping device according to claim 2, wherein the first end of the coupling member is fastened to the distal end of the actuating wire by welding.

4. The clipping device according to claim 3, wherein the first end of the coupling member is fastened to the distal end of the actuating wire by laser welding.

5. The clipping device according to claim 2, wherein the first end of the coupling member is fastened to the distal end of the actuating wire by pressing.

6. The clipping device according to claim 5, wherein the first end of the coupling member is fastened to the distal end of the actuating wire by caulking.

7. The clipping device according to claim 1, wherein
   the first end of the coupling member includes a hole, and
   the first end of the coupling member is attached to the actuating wire by hooking the actuating wire in the hole.

8. The clipping device according to claim 7, wherein the actuating wire is turned back in a portion to be hooked in the hole.

9. The clipping device according to claim 1, wherein
   the coupling member including the first end and the second end is a single piece construction,
   the first end of the coupling member permanently set to the actuating wire, and
   the second end of the coupling member couples to the tissue clip and is beyond repair after applying the tissue clip.

10. The clipping device according to claim 1, wherein the second end of the coupling member include a hook in which the tissue clip is hooked.

11. The clipping device according to claim 1, further comprising an operation unit for exercising a pulling action on the actuating wire to exert the force in the proximal direction at the first end of the coupling member,
    wherein the operation unit is provided with a slider that is coupled to the proximal end of the actuating wire and is guided so as to be slidable in a longitudinal direction.

12. The clipping device according to claim 1, further comprising:
    an insertion tube that is fitted over the sheath member and movable longitudinally relative to the sheath member,
    a first operation unit mounted in the area of the proximal end of the insertion tube for longitudinally moving the insertion tube relative to the sheath member, and
    a second operation unit for exercising a pulling action on the actuating wire to exert the force in the proximal direction at the first unit of the coupling member, wherein the second operation unit is provided with a slider that is coupled to the proximal end of the actuating wire and is guided so as to be slidable in longitudinal direction.

13. The clipping device according to claim 12, wherein the insertion tube is provided with raised portions at its inner surface and/or its outer surface.

14. The clipping device according to claim 1, further comprising a lubricant disposed on an outer surface of the actuating wire.

15. The clipping device according to claim 14, wherein the lubricant disposed on the outer surface of the actuating wire is silicone oil.

16. The clipping device according to claim 1, wherein the clipping device is arranged in a packaging unit.

17. The clipping device according to claim 1, further comprising a first operation unit mounted in the area of a proximal end of an insertion tube of an endoscope for longitudinally moving the insertion tube relative to the sheath member, as well as a second operation unit for exercising a pulling action on the actuating wire to exert the force in the proximal direction at the first end of the coupling member,
wherein the second operation unit is provided with a slider that is coupled to the proximal end of the actuating wire and is guided so as to be slidable in a longitudinal direction.

18. A clipping device to be used in combination with an endoscope having a channel, the device comprising:
an insertion tube to be inserted in the body of the patient through the channel;
a sheath member to be inserted in the insertion tube so as to be longitudinally movable relative to the insertion tube;
an actuating wire received in the sheath member so as to be longitudinally movable relative to the sheath member;
a clip unit attached to the clipping device in advance and having a tissue clip for clipping in the body of the patient and a coupling member including a first end fastened to a distal end of the actuating wire to be immovable in an axial direction of the actuating wire and a direction deviating from the axial direction and a second end attached to the tissue clip;
an operation unit for exercising a pulling action on the actuating wire to exert the force in the proximal direction at the first end of the coupling member,
wherein:
when applying the tissue clip, the first end of the coupling member is kept fastened to the actuating wire to be immovable in an axial direction of the actuating wire and a direction deviating from the axial direction, and the second end of the coupling member is deformable upon exertion of a force in a proximal direction at the first end of the coupling member due to the operation unit so as to prevent a subsequent attachment of the second end to another tissue clip.

19. The clipping device according to claim 18, wherein the first end of the coupling member is directly fastened to a peripheral surface of the distal end of the actuating wire.

20. The clipping device according to claim 19, wherein the first end of the coupling member is fastened to the distal end of the actuating wire by welding.

21. The clipping device according to claim 19, wherein the first end of the coupling member is fastened to the distal end of the actuating wire by pressing.

22. The clipping device according to claim 18, wherein
the coupling member including the first end and the second end is a single piece construction,
the first end of the coupling member permanently set to the actuating wire, and
the second end of the coupling member couples to the tissue clip and is beyond repair after applying the tissue clip.

23. A method for clipping tissue using a clipping device in combination with an endoscope having a channel, the method comprising:
inserting an insertion tube in the body of the patient through the channel;
inserting a sheath member in the insertion tube so as to be longitudinally movable relative to the insertion tube;
receiving an actuating wire in the sheath member so as to be longitudinally movable relative to the sheath member;
providing a clip unit attached to the clipping unit in advance and having a tissue clip for clipping in the body of the patient;
attaching a first end of a coupling member to a distal end of the actuating wire to be immovable in an axial direction of the actuating wire and a direction deviating from the axial direction;
attaching a second end of the coupling member to the tissue clip;
projecting the tissue clip from a distal end of the insertion tube;
pulling on the actuating wire to exert a force in the proximal direction at the first end of the coupling member,
when applying the tissue clip, keeping the first end of the coupling member fastened to the actuating wire to be immovable in an axial direction of the actuating wire and a direction deviating from the axial direction; and
deforming the second end of the coupling member upon exertion of the force thereby preventing a subsequent attachment of another tissue clip to the coupling member.

24. A tissue clipping method comprising:
inserting a sheath member in a body of a patient;
receiving an actuating wire in the sheath member so as to be longitudinally movable relative to the sheath member;
arranging a clip unit attached to the clipping device in advance and having a tissue clip for clipping in the body of the patient and a coupling member at a distal end of the actuating wire;
making the coupling member, including a first end fastened to the distal end of the actuating wire, immovable in an axial direction of the actuating wire and a direction deviating from the axial direction;
attaching a second end of the coupling member to the tissue clip; and
when applying the tissue clip, deforming the second end of the coupling member upon exertion of a force in a proximal direction at the first end of the coupling member that is greater than a predetermined amount so as to prevent a subsequent attachment of the second end to another tissue clip.

* * * * *